(12) United States Patent
Maydanich

(10) Patent No.: US 6,370,881 B1
(45) Date of Patent: Apr. 16, 2002

(54) X-RAY IMAGER COOLING DEVICE

(75) Inventor: Fyodor Maydanich, Wauwatosa, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/782,115

(22) Filed: Feb. 12, 2001

(51) Int. Cl.[7] ................................................ F25B 21/02
(52) U.S. Cl. ...................................... 62/3.2; 250/370.14
(58) Field of Search ............................... 62/3.2, 3.3, 3.4, 62/3.7, 259.2; 378/37; 250/370.14, 208.1

(56) References Cited

U.S. PATENT DOCUMENTS 4,996,413 A * 2/1991 McDaniel et al. ........ 250/208.1
5,596,200 A * 1/1997 Sharma et al. .......... 250/370.14
6,201,249 B1 * 3/2001 Yamayoshi ............. 250/370.11

* cited by examiner

*Primary Examiner*—William Doerrler
*Assistant Examiner*—Melvin Jones

(57) ABSTRACT

A cooling mechanism and device for digital x-ray imagers. The x-ray imager is positioned on a thermal spreader plate which in turn is positioned on a thermoelectric cooler. The thermal spreader plate is the prime thermally conductive interface between the x-ray imager and the cooled surface of the thermoelectric heat pump/cooler. The device maintains the x-ray imager at a constant temperature with a small and consistent uniform temperature gradient across its bottom surface.

8 Claims, 1 Drawing Sheet

X-RAY IMAGER COOLING DEVICE

TECHNICAL FIELD

The present invention relates to x-ray imagers and more particularly to a cooling mechanism for digital x-ray imagers.

BACKGROUND OF THE INVENTION

X-ray systems include a source for projecting an x-ray beam toward an object to be analyzed, such as a medical patient. After the beam passes through the patient, an image intensifier converts the radiation into a signal. With solid state digital x-ray detectors, the photodiode detector elements produce electrical signals which correspond to the brightness of the picture element in the x-ray image projected onto the detector. The signals from the detector elements are read out individually and digitized for further image processing, storage and display, typically by a computer.

For accurate and consistent results, an x-ray imager needs to be operated within a pre-specified temperature range and with a constant uniform temperature gradient across its surface. Current systems employ a liquid cooling method in order to accomplish this. The cooling fluids utilized in these systems, however, are chemically aggressive, and the systems for pressurization of the cooling fluid are mechanical and often unreliable.

Thus, a need exists for improved systems and devices for cooling digital x-ray imagers for x-ray systems, such as those used for medical diagnostic imaging.

SUMMARY OF THE INVENTION

It is an object of the present invention to provide an improved cooling process and device for digital x-ray imagers, particularly, although not exclusively, for use in medical diagnostic imaging. It is another object of the present invention to eliminate the use of chemically aggressive cooling fluids in medical facilities as well as unreliable means of liquid pressurization and transport.

These objects are met with the present invention, and the problems with existing cooling systems are overcome. In accordance with the present invention, an improved cooling device for a digital x-ray imager is provided which includes a thermal spreader plate and a thermal electric heat pump. The thermal spreader plate includes a vacuum vessel vapor chamber, which is the prime thermal conductive interface positioned on the x-ray imager lower surface. The thermoelectric heat pump is used as a cooling device and is attached to the thermal spreader plate and held at the required temperature. The digital x-ray imager is positioned on the surface of the thermal spreader plate (opposite to the cooling device) and held at a constant temperature. This provides a constantly uniform temperature gradient across the imager.

Other benefits, features, and advantages of the present invention will become apparent from the following description of the invention when taken in view of the attached drawings and appended claims.

DESCRIPTION OF THE PREFERRED EMBODIMENT(S)

Figure 1:
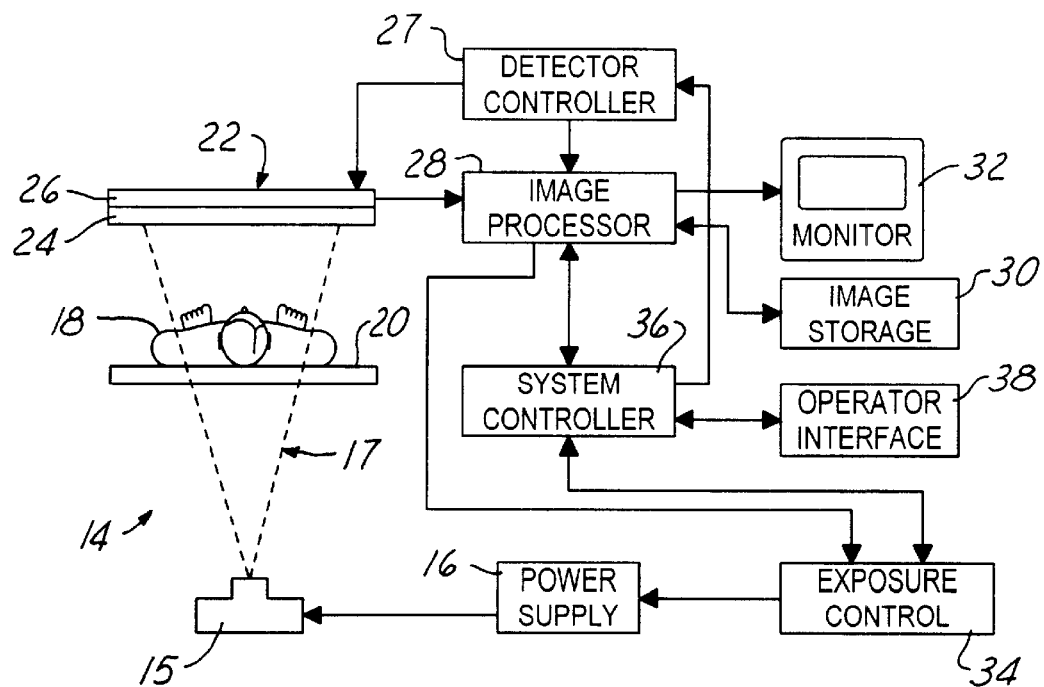
FIG. 1 is a schematic diagram of an x-ray system utilizing the present invention.

FIG. 1 shows a representative x-ray system in which the present invention can be utilized. An x-ray apparatus 14 includes a x-ray tube 15 by which, when excited by high voltage power supply 16, emits an x-ray beam 17. As illustrated, the x-ray beam is directed toward a patient 18 lying on an x-ray transmissive table 20. The portion of the beam which is transmitted through the table and the patient impinges upon an x-ray detector designated 22. The x-ray detector 22 comprises a scintillator 24 that converts the x-ray photons to lower energy photons in the visible spectrum. Contiguous with the scintillator 24 is a photo detector array 26 which converts the light photons into an electrical signal. A detector controller 27 contains electronics for operating the detector array to acquire an image and to read out the signal from each photo detector element.

The output signal from the photo detector array 26 is coupled to an image processor 28 that includes circuitry for processing and enhancing the x-ray image signal. The processed image then is displayed on a video monitor 32 and may be archived in an image storing device 30. The image processor 28 additionally produces a brightness control signal that is applied to an exposure control circuit 34 to regulate the power supply 16 and thereby the x-ray exposure.

The overall operation of the x-ray apparatus 14 is governed by a system controller 36, which receives commands from an x-ray technician or the like through an operator interface panel 38. The system controller 36 is typically a computer.

As indicated, the x-ray system described above is merely representative of the various types of x-ray systems in which the present invention can be utilized. The present invention can be utilized in any type of x-ray system in which a digital x-ray imager is utilized. This includes systems in which the patient is situated in a standing position between the x-ray tube and the imager. One digital radiography system of this type is the REVOLUTION system of General Electric Medical Systems.

Although the present invention is described herein relative to use for medical diagnostic imaging, it is to be understood that the present invention can be used in any x-ray system for any purpose. In this regard, x-ray systems are currently in use for security systems, such as in an airport or governmental building, and for non-destructive testing of structures and objects, such as bridges and buildings.

In order to obtain an x-ray image with a digital x-ray imager, both offset and gain corrections are necessary to account for the different responses of the individual pixels in the imager. The response of the pixels in the digital x-ray imager to x-rays is generally dependent on the temperature. In order to minimize imaging artifacts, the digital x-ray imager therefore should be held at a certain temperature with a constant uniform temperature gradient across the imager surface.

Figure 2:
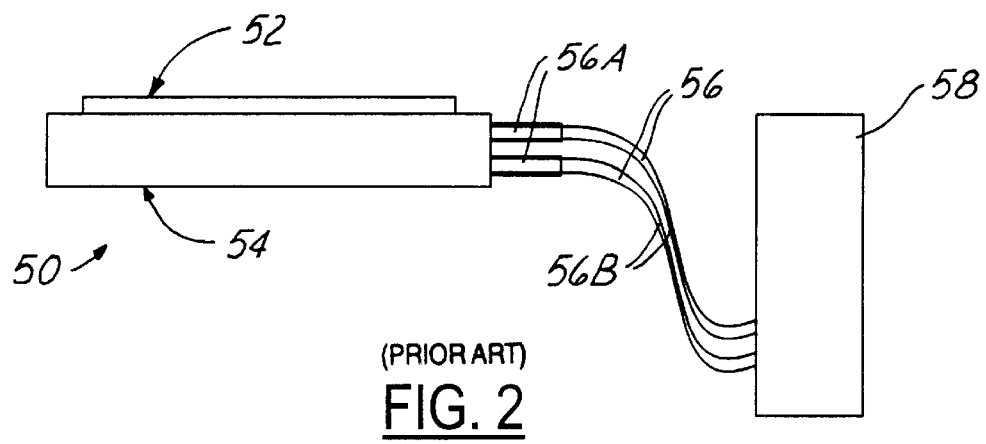
FIG. 2 is a schematic diagram of a prior art cooling system.

A prior art cooling system for achieving the requisite cooling of an x-ray imager is shown, for example, in FIG. 2. The cooling system which is indicated generally by the reference numeral 50 includes a digital x-ray imager 52, a cold plate 54, connecting elements or conduits 56, and a cooling mechanism 58. The cold plate 54 maintains a thermally conductive interface against the lower surface of the x-ray imager 52. The conduits 56 include hollow tubular members 56A, which are embedded in the cold plate 54, as well as elongated flexible hoses 56B, which connect the hollow tubular members to the cooling device 58.

The cooling device 58, often called a "chiller," is used to provide liquid cooling material for circulation via the conduits 56 into and through the cold plate 54. The cooling device 58 is typically remotely located from the digital x-ray system and has a system or mechanism (not shown) which pressurizes and transports the cooling liquid to the cold plate via a mechanical pumping mechanism. Typically, chemically aggressive fluids such as the "Digital Detector Conditioner Coolant" from Aqua Science, are utilized in the prior art cooling mechanism 50. These fluids are typically toxic and reactive and are a concern when used with respect to medical facilities. Also, the mechanical pumping system used with prior art methods, such as the prior art cooling system 50 described herein, have low degrees of reliability due to the mechanical mechanisms utilized.

Figure 3:
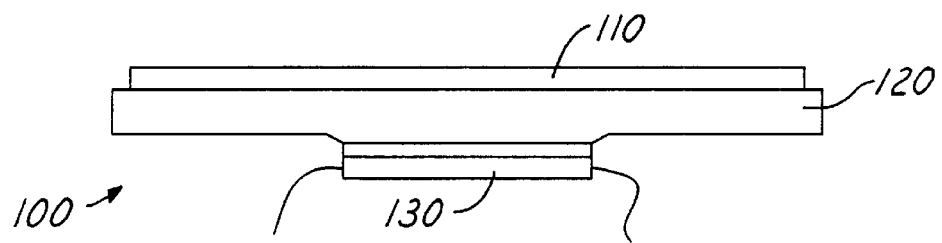
FIG. 3 is a schematic diagram of the inventive cooling system in accordance with the present invention.

A representative mechanism or device utilizing the present invention is shown schematically in FIG. 3 and referred to generally by the reference numeral 100. The device 100 includes a digital x-ray imager 110, a thermal spreader plate 120, and a thermoelectric heat pump 130. The digital x-ray imager 110 can be of any conventional type, such as the Innova 2000 by General Electric Medical Systems. The digital imager 110 includes an amorphous silicon array positioned on a glass substrate. Contact fingers from the silicon array connect it to a contact lead for an electronic readout. A scintillator is positioned over the silicon array that converts the light photons from the x-ray beam into an electrical signal for detection by the array.

The amorphous silicon array includes a plurality of detector elements arranged in a two-dimensional array in columns and rows. Each detector element includes a photodiode and a thin film transistor. The photodiodes intercept a portion of the light produced by the scintillator and have large capacitance which allow them to store the electrical charge resulting from the photon excitation. The photo diode array absorbs light and converts it into an electrical charge. Each photodiode represents a pixel or picture element. The charge at each pixel is connected through the electronic read out and turned into digital data sent to an image processor. The processor, which typically is a computer, then develops the digital data into a usable image. The digital detector has a high detective quantum efficiency (DQE) which has low noise and high contrast. This process is described in more detail in U.S. Pat. No. 4,996,413, the disclosure which is hereby incorporated by reference herein.

The thermal spreader plate 120 is comprised of a vapor chamber which acts as a vacuum vessel with a saturated wick structure lining the inside walls. As a thermal source is applied to the base of the plate, the working fluid, which typically is water, immediately vaporizes at that location. The vapor then moves to fill the vacuum. When the vapor comes into contact with the cooler wall surface, it condenses. The condensation releases the latent heated vaporization of the fluid. The condensed fluid then returns to the thermal source via capillary action in the wick structure.

The capillary action enables the thermal spreader plate to work in any orientation with respect to gravity. In this manner, the thermal plate can be positioned in any direction (horizontal, vertical, etc.) depending on the particular x-ray system utilized.

The thermal resistance normally associated with the spreading of water vapor is negligible in a thermal spreader plate. This provides an effective means for spreading the heat from a concentrated energy source to a larger surface. As a working fluid, the high latent heated vaporization of water spreads more heat with less fluid flow. Also, the high thermal conductivity of water minimizes the Delta T associated with conduction through the wick. Due to the thermal spreader plate's negligible heat "spreading resistance," a low and consistently uniform temperature gradient across the bottom surface of the x-ray imager is achieved.

In accordance with the present invention, a conventional thermal spreader plate can be utilized so long as it meets the objects and purposes of the invention. Thermal spreader plates of Thermacore Int'l, Inc., Lancaster, Pa., can be utilized for this purpose.

The thermoelectric heat pump 130 is the main cooling device for the system. Heat pumps utilize the basic laws of thermal dynamics as do any devices involved in the transfer of heat energy. The heat pump preferably is a solid state device powered by direct current and is used for cooling by reversing the direction of the current flow.

Thermoelectric heat pumps which can be utilized in the present invention include the line of Thermoelectic coolers (TECs) by Melcor in Trenton, N.J.

The cooled surface of the thermoelectric heat pump 130 (or "cooler") is attached directly to the evaporator plate of the thermal spreader 120. The thermoelectric heat pump is held at the required temperature by a temperature control utilizing a closed loop method. The temperature of the thermally conductive thermal spreader evaporator plate will be approximately the temperature of the cold surface of the thermoelectric heat pump 130.

To achieve the vaporization of the working fluid in the thermal spreader plate 120 at any given temperature, the vapor chamber of the thermal plate 120, which acts as a vacuum vessel, is set at a pre-specified pressure. In this regard, the boiling temperature of the working fluid is a function of the ambient pressure inside of the vapor chamber.

The digital x-ray imager 110 is positioned on the outer surface of the condenser plate of the thermal spreader plate 120. Due to thermal conduction and the low heat "spreader resistance," the bottom surface of the imager 110 is held at a constant temperature close to the boiling temperature of the working fluid. A small and consistently uniform temperature gradient is provided across the bottom surface of the detector.

With the present invention, an improved device and mechanism for cooling digital x-ray imagers is provided. This provides a consistent and effective cooling mechanism without the use of undesirable chemical fluids and unreliable mechanisms for pressurization and transport of the cooling liquid.

While the invention has been described in connection with one or more embodiments, it is to be understood that the specific mechanisms and techniques which have been described are merely illustrative of the principles of the invention. Numerous modifications may be made to the methods and apparatus described without departing from the spirit and scope of the invention as defined by the appended claims.

What is claimed is:

1. A cooling mechanism for a digital x-ray imager comprising:
    a thermal spreader plate adapted for attachment to the x-ray imager; and
    a thermoelectric cooler attached to said thermal spreader plate.

2. A cooling mechanism as recited in claim 1 wherein the imager has a bottom surface, said thermal spreader plate has an upper and lower surface, and the thermoelectric cooler has a principal cold surface, and wherein said upper surface of said thermal spreader plate is positioned in direct contact with the bottom surface of the imager, and said principal cold surface of said thermoelectric cooler is positioned in direct contact with the lower surface of said thermal spreader plate.

3. The cooling mechanism as recited in claim 1 wherein said thermal spreader plate comprises a base plate member, an upper plate member, a vapor chamber, a working fluid and a saturated wick structure, and whereby said thermal spreader plate when exposed to a constant temperature source on said base plate member provides a constant uniform temperature uniformly across said upper plate member.

4. The cooling mechanism as recited in claim 1 wherein said thermoelectric cooler is a heat pump.

5. A method for providing cooling to a digital x-ray imager comprising:

positioning a thermal spreader plate on one surface of the x-ray imager, said thermal spreader plate having a base plate member and an upper plate member;

positioning a thermoelectric cooler on said base plate member; and cooling said thermoelectric cooler to a controlled uniform temperature.

6. The method as recited in claim 5 wherein said thermoelectric cooler is a heat pump.

7. The method as recited in claim 5 wherein said thermal spreader plate further includes a vapor chamber, a working fluid and a saturated wick structure.

8. The method as recited in claim 5 wherein said thermal spreader plate provides a constant temperature uniformly across said upper plate member and in turn provides a constant temperature gradient to the digital x-ray imager.

\* \* \* \* \*